(12) United States Patent
Sumikawa et al.

(10) Patent No.: US 10,640,484 B2
(45) Date of Patent: May 5, 2020

(54) METHOD FOR PRODUCING (R)-5-(3,4-DIFLUOROPHENYL)-5-[(3-METHYL-2-OXOPYRIDIN-1(2H)-YL) METHYL]IMIDAZOLIDINE-2,4-DIONE AND INTERMEDIATE FOR PRODUCING SAME

(71) Applicant: KAKEN PHARMACEUTICAL CO., LTD., Tokyo (JP)

(72) Inventors: Yoshitake Sumikawa, Kyoto (JP); Noriyuki Kamei, Kyoto (JP); Shingo Todo, Tokyo (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/335,095

(22) PCT Filed: Sep. 21, 2017

(86) PCT No.: PCT/JP2017/034151
§ 371 (c)(1),
(2) Date: Mar. 20, 2019

(87) PCT Pub. No.: WO2018/056373
PCT Pub. Date: Mar. 29, 2018

(65) Prior Publication Data
US 2019/0276428 A1 Sep. 12, 2019

(30) Foreign Application Priority Data
Sep. 23, 2016 (JP) .................. 2016-185325

(51) Int. Cl.
*C07D 401/06* (2006.01)
(52) U.S. Cl.
CPC .................. *C07D 401/06* (2013.01)
(58) Field of Classification Search
CPC .................................. C07D 401/06
See application file for complete search history.

(56) References Cited

U.S. PATENT DOCUMENTS

| 5,180,733 A | 1/1993 | Basha et al. |
| 5,686,628 A | 11/1997 | Veale et al. |
| 2015/0166506 A1 | 6/2015 | Kamei et al. |
| 2016/0130248 A1 | 5/2016 | Kamei et al. |

FOREIGN PATENT DOCUMENTS

| JP | 4-235167 A | 8/1992 |
| JP | 10-513173 A | 12/1998 |
| WO | 2013/085016 A1 | 6/2013 |
| WO | 2014/196623 A1 | 12/2014 |

OTHER PUBLICATIONS

Sung, et al., "Preparation of 2R, 3S, 2'R-Nadolol Enantiomer Using S-(−)-Menthyl Chloroformate as a Chiral Derivatizing Reagent", Archives of Pharmacal Research, 2010, vol. 33, No. 9, pp. 1301-1306 (6 pages total).

Isherwood, et al., "An efficient synthesis of (7S,10R)-2-bromo-5,6,7,8,9,10-hexahydro-7,10-epiminocyclohepta [b] indole: application in the preparation and structural confirmation of a potent 5-HT$_6$ antagonist", Elsevier, Tetrahedron: Asymmetry, 2012, vol. 23, pp. 1522-1527 (6 pages total).

*Primary Examiner* — David K O'Dell
(74) *Attorney, Agent, or Firm* — Sughrue Mion, PLLC (57) ABSTRACT

A method for producing (R)-5-(3,4-difluorophenyl)-5-[(3-methyl-2-oxopyridin-1(2H)-yl)methyl]imidazolidine-2,4-dione, the method comprising, (a) a step for isolating an isomer represented by formula (2) from a mixture of isomers represented by formula (1), and (b) a step for obtaining (R)-5-(3,4-difluorophenyl)-5-[(3-methyl-2-oxopyridin-1 (2H)-yl)methyl]imidazolidine-2,4-dione by removing the menthyloxycarbonyl group from the compound represented by formula (2), which was isolated in step (a).

3 Claims, 4 Drawing Sheets

METHOD FOR PRODUCING (R)-5-(3,4-DIFLUOROPHENYL)-5-[(3-METHYL-2-OXOPYRIDIN-1(2H)-YL)METHYL]IMIDAZOLIDINE-2,4-DIONE AND INTERMEDIATE FOR PRODUCING SAME

CROSS REFERENCE TO RELATED APPLICATIONS

This application is a National Stage of International Application No. PCT/JP2017/034151, filed Sep. 21, 2017, claiming priority to Japanese Patent Application No. 2016-185325, filed Sep. 23, 2016.

TECHNICAL FIELD

The present invention relates to a method of producing (R)-5-(3,4-difluorophenyl)-5-[(3-methyl-2-oxopyridin-1(2H)-yl)methyl]imidazolidin-2,4-dione and an intermediate for the production thereof.

BACKGROUND ART

It has been reported that (+)-5-(3,4-difluorophenyl)-5-[(3-methyl-2-oxopyridin-1(2H)-yl)methyl]imidazolidin-2,4-dione has an excellent inhibitory activity of a tumor necrosis factor alpha (TNF-α) converting enzyme (TACE) and is useful as a therapeutic and prophylactic agent for diseases involving TNF-α (Patent Literature 1).

In Patent Literature 1, the following two methods are disclosed as methods for producing the optically pure (+)-5-(3,4-difluorophenyl)-5-[(3-methyl-2-oxopyridin-1(2H)-yl)methyl]imidazolidin-2,4-dione.

Scheme 1

(wherein X represents a chlorine atom, a bromine atom, or an iodine atom; and the asterisk (*) signifies an optically pure form)

Scheme 2

(+)-(I)

(In the formulae, the asterisk (*) signifies an optically pure form)

The production method of scheme 1 is a method of optically dividing a racemate by chiral column chromatography, and from the viewpoint of production efficiency it is hard to say that this method is suitable for production on a commercial scale. In addition, in the production method of scheme 2, the (R)-tert-butanesulfinamide used as an asymmetric auxiliary group is expensive and it involves reactions that produce impurities that are difficult to remove, such as impurities derived from a titanium reagent, and hence from the viewpoint of manufacturing cost and work efficiency, it would be undesirable to apply this method on a commercial scale.

CITATION LIST

Patent Literature

[Patent Literature 1] International Publication No. WO 2014/196623

SUMMARY OF INVENTION

Technical Problem

It is an object of the present invention to provide a novel method of producing (R)-5-(3,4-difluorophenyl)-5-[(3-methyl-2-oxopyridin-1(2H)-yl)methyl]imidazolidin-2,4-dione that can be suitably applied on a commercial scale.

Solution to Problem

As a result of a diligent research into methods of producing (R)-5-(3,4-difluorophenyl)-5-[(3-methyl-2-oxopyridin-1(2H)-yl)methyl]imidazolidin-2,4-dione, the present inventors discovered that an isomer represented by formula (2) could be easily separated from a mixture of isomers represented by formula (1), and that by removing a menthyloxycarbonyl group of the compound represented by formula (2), (R)-5-(3,4-difluorophenyl)-5-[(3-methyl-2-oxopyridin-1 (2H)-yl)methyl]imidazolidin-2,4-dione could be efficiently produced, thereby completing the present invention. Herein, the novel compound represented by formula (2) is an important intermediate in the production method of the present invention.

Specifically, the present invention relates to each of the following.

[1] A method of producing (R)-5-(3,4-difluorophenyl)-5-[(3-methyl-2-oxopyridin-1(2H)-yl)methyl]imidazolidin-2,4-dione, the method comprising:

(a) a step of separating an isomer represented by the following formula (2)

from a mixture of isomers represented by the following formula (1); and (b) a step of removing menthyloxycarbonyl group of the compound represented by formula (2) separated in step (a) to obtain (R)-5-(3,4-difluorophenyl)-5-[(3-methyl-2-oxopyridin-1(2H)-yl)methyl]imidazolidin-2,4-dione.

[2] The method according to [1], wherein the mixture of isomers represented by formula (1) is obtained from a racemate (±)-5-(3,4-difluorophenyl)-5-[(3-methyl-2-oxopyridin-1(2H)-yl)methyl]imidazolidin-2,4-dione.

[3] (R)-(1R,2S,5R)-2-isopropyl-5-methylcyclohexyl 4-(3,4-difluorophenyl)-4-[(3-methyl-2-oxopyridin-1(2H)-yl)methyl]-2,5-dioxoimidazolidine-1-carboxylate.

Advantageous Effects of the Invention

According to the present invention, (R)-5-(3,4-difluorophenyl)-5-[(3-methyl-2-oxopyridin-1(2H)-yl)methyl]imidazolidin-2,4-dione can be efficiently produced even for commercial scale manufacture.

DESCRIPTION OF EMBODIMENTS

The present invention is described in detail.

The production method of the present invention is a method for producing, as illustrated by the below scheme, (R)-5-(3,4-difluorophenyl)-5-[(3-methyl-2-oxopyridin-1(2H)-yl)methyl]imidazolidin-2,4-dione, wherein the method comprises a "step (a)" of separating an isomer represented by formula (2) (hereinafter may be abbreviated as "compound (2)") from a mixture of isomers represented by formula (1) (hereinafter may be abbreviated as "isomer mixture (1)") and a "step (b)" of removing a menthyloxycarbonyl group from compound (2) to obtain (R)-5-(3,4-difluorophenyl)-5-[(3-methyl-2-oxopyridin-1(2H)-yl)methyl]imidazolidin-2,4-dione.

(1)

(2)

(R)-5-(3,4-difluorophenyl)-5-[(3-methyl-2-oxopyridin-1(2H)-yl)methyl]imidazolidin-2,4-dione Meanwhile, the inventors of the present invention identified the absolute stereoconfiguration of the (+)-5-(3,4-difluorophenyl)-5-[(3-methyl-2-oxopyridin-1(2H)-yl)methyl]imidazolidin-2,4-dione described in Patent Literature 1 and found it to be the (R) configuration. Specifically, in the present specification, (R)-5-(3,4-difluorophenyl)-5-[(3-methyl-2-oxopyridin-1(2H)-yl)methyl]imidazolidin-2,4-dione and (+)-5-(3,4-difluorophenyl)-5-[(3-methyl-2-oxopyridin-1(2H)-yl)methyl]imidazolidin-2,4-dione represent the same compound.

The "isomer mixture (1)" is a mixture of (R)-(1R,2S,5R)-2-isopropyl-5-methylcyclohexyl 4-(3,4-difluorophenyl)-4-[(3-methyl-2-oxopyridin-1(2H)-yl)methyl]-2,5-dioxoimidazolidine-1-carboxylate (hereinafter may be abbreviated as "compound (1)-(R)" or "compound (2)") and (S)-(1R,2S,5R)-2-isopropyl-5-methylcyclohexyl 4-(3,4-difluorophenyl)-4-[(3-methyl-2-oxopyridin-1(2H)-yl)methyl]-2,5-dioxoimidazolidine-1-carboxylate (hereinafter may be abbreviated as "compound (1)-(S)"). More specifically, the diastereomeric excess (d.e.) of that mixture is 0 to 40%.

Compound (1)-(R) (compound (2)) and compound (1)-(S) are both novel substances, as is isomer mixture (1), which is a mixture of these compounds.

In the present invention, the term "separating an isomer" means performing a process such that the "mixture of isomers" is in a state in which the excess ratio of one isomer is higher. It is preferable for the diastereomeric excess to be 70 to 100%, and more preferable for the diastereomeric excess to be even closer to 100%.

The production method of the present invention is based on the use of a mixture of diastereomers which are easily separated owing to the inclusion of a specific asymmetric auxiliary group that enables optically active substances to be separated from each other. Therefore, there may exist an asymmetric auxiliary group capable of achieving the object of the present invention other than a menthyloxycarbonyl group, which is the leaving group used in the present invention.

Steps and Reaction Conditions of Production Method of Present Invention

[Step (a)]

Step (a) is a step represented by the following scheme for separating compound (2) from a mixture of isomers represented by formula (1).

In this step, the isomer mixture (1) may be as a composition comprising other components. Examples of such a composition include the reaction solution when the isomer mixture (1) is synthesized, a concentrate of that reaction solution, an extract from that solution, a solution, emulsion, or suspension containing the isomer mixture (1), and the like.

The method for separating compound (2) from the isomer mixture (1) can be carried out using methods ordinarily employed in organic chemistry. For example, the separation can be carried out by a method using column chromatography, high-performance liquid chromatography, or the like. Further, the separation can be carried out more easily by recrystallization, slurring and washing, crystallization, or solid-liquid separation.

Separation by recrystallization can be carried out regardless of the mode of the isomer mixture (1). After the isomer mixture (1) is dissolved in a solvent, compound (2) is precipitated.

The solvent to be used in recrystallization is preferably methanol, ethanol, 2-propanol, acetonitrile, or the like. These solvents may be used alone or in combination of two or more kinds. Further, a mixed solvent of the above-mentioned solvents and water may be used. As the recrystallization method, conventional recrystallization methods can be used. For example, there can be used a method in which the isomer mixture (1) is dissolved in a solvent and then compound (2) is precipitated by a cooling, or a method in which the isomer mixture (1) is dissolved in a solvent and then the solvent is distilled off to precipitate compound (2). In addition, a combination of these methods may be used. After the isomer mixture (1) is mixed with the solvent, the isomer mixture (1) may be dissolved by heating. The amount to use of the solvent is not limited, and depends on the solvent to be used; for example, for 1 kg of the isomer mixture (1), it is preferable to use 18 to 30 L of solvent.

Separation by slurring and washing is carried out by, when the isomer mixture (1) used in step (a) is a solid, mixing the isomer mixture (1) with the solvent to form a slurry. The solvent used for slurring and washing is preferably normal heptane, toluene, methanol, acetonitrile, ethyl acetate, diisopropyl ether, 1,4-dioxane, 1,2-dimethoxyethane, cyclopentyl methyl ether, or the like. These solvents may be used alone or in combination of two or more kinds. Slurring and washing can be carried out at any temperature as long as it is equal to or lower than the boiling point of the solvent. For example, slurring and washing may be carried out at room temperature or may be carried out with heating. The amount to use of the solvent is not limited, and depends on the solvent to be used; for example, for 1 kg of the isomer mixture (1), it is preferable to use 3 to 20 L, and more preferably 5 to 15 L, of solvent.

Separation by crystallization is carried out by, when the isomer mixture (1) used in step (a) is a composition containing other components, mixing an appropriate solvent with the composition. Examples of the composition include a reaction solution obtained by synthesizing the isomer mixture (1) and the like. The solvent to be mixed is preferably methanol, acetonitrile, or water. These solvents can be used alone or two or more kinds of solvents can be used in combination.

Separation by solid-liquid separation is carried out by, when the isomer mixture (1) used in step (a) is a suspension in which compound (2) is precipitated, collecting compound (2) from the suspension. Examples of the suspension include a reaction solution in which the produced compound (2) has precipitated under the reaction conditions for synthesizing the isomer mixture (1), a solution obtained by concentrating that reaction solution, and the like. Before collecting compound (2) by filtration, the suspension may be mixed with an appropriate solvent for the purpose of, for example, improving filtration properties and improving the yield. The solvent to be mixed is not particularly limited, but, for example, methanol, acetonitrile, or water is preferable. These solvents can be used alone, or two or more kinds of solvents can be used in combination.

The diastereomeric excess of the separated product obtained by recrystallization, slurring and washing, crystallization, or solid-liquid separation can be further increased by a reprocessing method. In the reprocessing method, the above-mentioned recrystallization or slurring and washing conditions can be applied. Although separation can be carried out by using just a single one of the above-mentioned methods, to achieve the desired diastereomeric excess, for example, the same method can be carried out twice or more, or two or more different methods can be carried out sequentially in a desired order. The diastereomeric excess of the separated product obtained in step (a) is preferably 70 to 100%, and more preferably as close to 100% as possible.

The temperature at which step (a) is carried out is not particularly limited, and step (a) can be carried out at room temperature. The time required for step (a) is preferably about 1 hour to about 3 days.

[Step (b)]

Step (b) is a step represented by the following scheme, in which the menthyloxycarbonyl group is removed from compound (2) to give (R)-5-(3,4-difluorophenyl)-5-[(3-methyl-2-oxopyridin-1(2H)-yl)methyl]imidazolidin-2,4-dione.

(2)

Step (b) →

(R)-5-(3,4-difluorophenyl)-5-[(3-methyl-2-oxopyridin-1(2H)-yl)methyl]imidazolidin-2,4-dione Here, the "menthyloxycarbonyl group" refers to a "(1R, 2S,5R)-2-isopropyl-5-methylcyclohexyloxycarbonyl group".

This step is carried out in the presence of an acid or a base. By subsequent purification, the target compound with higher purity can be obtained.

The method for removing the menthyloxycarbonyl group is not particularly limited, and can be carried out by a method well known to those skilled in the art as a reaction for removing an asymmetric auxiliary group. For example, the target compound (R)-5-(3,4-difluorophenyl)-5-[(3-methyl-2-oxopyridin-1(2H)-yl)methyl]imidazolidin-2,4-dione can be obtained by a method including a step of mixing compound (2) with an acid or a base.

When the reaction in this step is carried out in the presence of an acid, the acid used in the reaction is not particularly limited as long as the intended reaction proceeds; preferably, the acid is hydrochloric acid, hydrobromic acid, sulfuric acid, methanesulfonic acid, trifluoromethanesulfonic acid, trifluoroacetic acid, or the like. The amount to use of the acid depends on the acid to be used, and can be appropriately set within a range that achieves the object of the present invention. The amount to use of the acid is, for example, 1 to 100 equivalents, and more preferably 5 to 50 equivalents, based on compound (2).

When the reaction in this step is carried out in the presence of a base, the base used in the reaction is not particularly limited as long as the intended reaction proceeds; preferably, the base is sodium methoxide or sodium ethoxide. The amount to use of the base is, for example, 1 to 20 equivalents, preferably 1 to 10 equivalents, and more preferably 1 to 5 equivalents, based on compound (2).

The reaction solvent used is not particularly limited as long as the intended reaction proceeds; preferably, the reaction solvent is ethyl acetate, toluene, methanol, ethanol, acetic acid, water, or the like. Further, depending on the acid or base to be used, the reaction may also be carried out under solvent-free conditions.

The reaction time in this step differs depending on the reaction temperature, the used acid, base, and solvent, and the like, but is usually 1 to 100 hours.

The compound obtained by the reaction may be purified according to a conventional method such as extraction, recrystallization, or chromatography.

The temperature at which step (b) is carried out differs depending on the acid or base used, and is not particularly limited; the reaction can be carried out at room temperature or with heating. Further, the time required for step (b) is preferably about 1 hour to about 3 days.

<Method for Producing Mixture of Isomers Represented by Formula (1)>

Next, a method of producing the mixture of isomers (isomer mixture (1)) represented by formula (1) will be described. The isomer mixture (1) is a substance to be used as a starting material in the production method of the present invention.

(1)

The method for producing the isomer mixture (1) is not particularly limited. For example, by reacting a mixture including (+)-5-(3,4-difluorophenyl)-5-[(3-methyl-2-oxopyridin-1(2H)-yl)methyl]imidazolidin-2,4-dione and (−)-5-(3,4-difluorophenyl)-5-[(3-methyl-2-oxopyridin-1(2H)-yl)methyl]imidazolidin-2,4-dione (e.g., (±)-5-(3,4-difluorophenyl)-5-[(3-methyl-2-oxopyridin-1(2H)-yl)methyl]imidazolidin-2,4-dione, which is a racemate represented in the following scheme), and a compound represented by the following general formula (3):

(3)

[wherein X represents a chlorine atom, an iodine atom, a bromine atom, a fluorine atom, an imidazolyl group, a 4-nitrophenyloxy group, or the like]

or a compound represented by the following general formula (4):

[wherein Y represents a leaving group such as an iodine atom, a bromine atom, methyl sulfate, or trifluoromethanesulfonate]

in the presence of a base, a menthyloxycarbonyl group can be introduced into each of the enantiomers constituting the mixture to produce the isomer mixture (1).

(±)-5-(3,4-difluorophenyl)-5-[(3-methyl-2-oxopyridin-1(2H)-yl)methyl]imidazolidin-2,4-dione can be obtained by the methods described in WO 2013/085016 or WO 2014/196623.

The amount to use for the compound represented by general formula (3) or the compound represented by general formula (4) relative to (±)-5-(3,4-difluorophenyl)-5-[(3-methyl-2-oxopyridin-1(2H)-yl)methyl]imidazolidin-2,4-dione is not particularly limited as long as the intended reaction proceeds, but it is preferably 1 to 1.5 equivalents, and more preferably 1.2 to 1.5 equivalents.

The base used in the production of the mixture of isomers represented by formula (1) is used in order to carry out the reaction of introducing the menthyloxycarbonyl group into each of the above-mentioned enantiomers more quickly.

The base to be used is not particularly limited as long as the intended reaction proceeds when either the compound represented by general formula (3) or the compound represented by general formula (4) is used. For example, bases such as triethylamine, N,N-diisopropylamine, pyridine, N-methylimidazole, N,N-dimethyl-4-aminopyridine, potassium tert-butoxide, sodium hydride, lithium diisopropylamide, and lithium hexamethyldisilazide may be used. Preferably, the base is triethylamine, N,N-diisopropylamine, pyridine, or N-methylimidazole, and more preferably triethylamine or N,N-diisopropylamine.

The amount to use of the base is not particularly limited as long as the intended reaction proceeds when either the compound represented by general formula (3) or the compound represented by general formula (4) is used. Preferably, the amount to use is 1 to 2 equivalents, and more preferably 1 to 1.5 equivalents.

The reaction solvent is not particularly limited as long as the intended reaction proceeds when either the compound represented by general formula (3) or the compound represented by general formula (4) is used. For example, N,N-dimethylformamide, tetrahydrofuran, ethyl acetate, acetonitrile, toluene, or the like can be used. These solvents can be used alone or in combination of two or more kinds. Depending on the base to be used, the reaction may also be carried out under solvent-free conditions.

The temperature at which the above-mentioned reaction is carried out is not particularly limited, and the reaction can be performed at room temperature. The reaction time of the reaction is preferably about 0.1 hour to about 1 day.

The isomer mixture (1) obtained in this reaction may be purified according to a conventional method such as chromatography, or may be used in step (a) as a composition such as the reaction solution, concentrate of the reaction solution, filtrate obtained by filtering the reaction solution, solution extracted from the reaction solution, or the like.

The compound represented by general formula (3) or the compound represented by general formula (4) may be used by isolating it or may be used in the form of a composition comprising other components. For example, a reaction solution in which the compound represented by general formula (3) has been prepared or a concentrate of such a reaction solution may be used, or a reaction solution in which the compound represented by general formula (4) has been prepared or a concentrate of such a reaction solution may be used.

The compound represented by general formula (3) or the compound represented by general formula (4) may be a commercially available product or a product obtained through preparation. These compounds can be prepared by a method known per se in this technical field.

The compound of general formula (4) can be obtained by, for example, reacting (1R,2S,5R)-2-isopropyl-5-methylcyclohexyl 1H-imidazole-1-carboxylate with a methylating agent. As the methylating agent, for example, methyl iodide, dimethyl sulfate, methyl trifluoromethanesulfonate, or the like can be used. The amount of the methylating agent to be used is not particularly limited as long as the intended reaction proceeds, but it is preferably 1 to 4 equivalents. The reaction solvent to be used is not particularly limited as long as the intended reaction proceeds; for example, acetonitrile, toluene, ethyl acetate, tetrahydrofuran, N,N-dimethylformamide, or the like can be used.

The prepared compound represented by general formula (3) or the prepared compound represented by general formula (4) may be a crude product obtained by distilling off the solvent, or a solution of the product may be used as is.

EXAMPLES

The present invention will now be specifically described with reference to examples, but the present invention is not limited to these examples in any way.

The $^1$H-NMR spectra shown below were recorded on either JNM-ECA 400 (400 MHz, JEOL) or AVANCE III HD 400 (400 MHz, Bruker BioSpin) using deuterated chloroform (CDCl$_3$) or deuterated dimethyl sulfoxide (DMSO-d$_6$ as a solvent and tetra methylsilane (TMS) as internal standard. Chemical shifts are shown in ppm and the J couplings are shown in Hz. The abbreviation "s" stands for singlet, "d" for doublet, "t" for triplet, "q" for quartet, and "m" for multiplet. Exactive (Thermo Fisher Scientific) was used for the mass spectrum (electrospray ionization: ESI-MS) measurement.

Production Example 1

Production of Mixture of Isomers Represented by Formula (1)—1 (Example Using Compound Represented by General Formula (3))

N,N-diisopropylamine (1.00 mL, 6.00 mmol) was added to a solution of (±)-5-(3,4-difluorophenyl)-5-[(3-methyl-2-oxopyridin-1(2H)-yl)methyl]imidazolidin-2,4-dione (1.00 g, 3.00 mmol) in N,N-dimethylformamide (6.0 mL), and the mixture was stirred under ice cooling. (−)-Menthyl chloroformate (828 µL, 3.90 mmol) was added dropwise, and the mixture was stirred at room temperature for 16 hours. The reaction solution was diluted with water and extracted with ethyl acetate. The organic layer was washed with saturated brine, and dried over anhydrous sodium sulfate. The solvent was distilled off under reduced pressure, and the residue was purified by column chromatography (silica gel) to obtain the isomer mixture (1) (1.35 g, 87% yield) as colorless solid.

Production Example 2

Production of Mixture of Isomers Represented by Formula (1)—2 (Example Using Crude Compound Represented by General Formula (4))

Dimethyl sulfate (569 µL, 5.99 mmol) was added dropwise to a solution of (1R,2S,5R)-2-isopropyl-5-methylcyclohexyl 1H-imidazole-1-carboxylate (1.50 g, 5.99 mmol) in acetonitrile (2.0 mL), and the mixture was stirred at room temperature for 22 hours. The solvent was distilled off under reduced pressure to give crude product of 1-{[((1R,2S,5R)-2-isopropyl-5-methylcyclohexyl)oxy]carbonyl}-3-methyl-1H-imidazol-3-ium methyl sulfate (2.26 g).
A solution of the obtained crude product of 1-{[((1R,2S,5R)-2-isopropyl-5-methylcyclohexyl)oxy]carbonyl}-3-methyl-1H-imidazol-3-ium methyl sulfate in in N,N-dimethylformamide (5.0 mL) was added to a solution of (±)-5-(3,4-difluorophenyl)-5-[(3-methyl-2-oxopyridin-1(2H)-yl)methyl]imidazolidin-2,4-dione (1.66 g, 4.98 mmol) and triethylamine (899 µL, 6.49 mmol) in N,N-dimethylformamide (5.0 mL), and the mixture was stirred at room temperature for 1.5 hours. Ethyl acetate (20.0 mL), normal hexane (5.0 mL) and water (10.0 mL) were added sequentially, and the organic layer was separated. The organic layer was washed successively with water and saturated brine, and dried over anhydrous sodium sulfate. The solvent was distilled off under reduced pressure, and the residue was purified by column chromatography (silica gel) to obtain the isomer mixture (1) (2.53 g, 99% yield) as colorless solid.

Production Example 3

Production of Mixture of Isomers Represented by Formula (1)—3 (Example Using Solution of Compound Represented by General Formula (4))

Dimethyl sulfate (285 µL, 3.00 mmol) was added dropwise to a solution of (1R,2S,5R)-2-isopropyl-5-methylcyclohexyl 1H-imidazole-1-carboxylate (750 mg, 3.00 mmol) in acetonitrile (1.0 mL), and the mixture was stirred at room temperature for 24 hours. The obtained reaction solution was added dropwise to a solution of (±)-5-(3,4-difluorophenyl)-5-[(3-methyl-2-oxopyridin-1(2H)-yl)methyl]imidazolidin-2,4-dione (1.66 g, 4.98 mmol) and triethylamine (899 µL, 6.49 mmol) in N,N-dimethylformamide (5.0 mL), and the mixture was stirred at room temperature for 30 minutes. Ethyl acetate (10.0 mL), normal hexane (2.5 mL) and water (5.0 mL) were added, and the organic layer was separated. The organic layer was washed successively with water and saturated brine, and dried over anhydrous sodium sulfate. The solvent was distilled off under reduced pressure, and the residue was purified by column chromatography (silica gel) to obtain the isomer mixture (1) (1.05 g, 87% yield) as colorless solid.

Example 1

Production of Compound (2)—1 (Production of Intermediate by Recrystallization)

Ethanol (30.0 mL) was added to the isomer mixture (1) (1.50 g, 2.90 mmol) and dissolved by stirring under reflux. The mixture was stirred for 12 hours while allowing to cool at room temperature. The precipitated solid was collected by filtration, washed with ethanol, and dried under reduced pressure to obtain compound (2) (547 mg, 37% yield, 97.0% d.e.) as colorless solid. $^1$H-NMR (400 MHz, CDCl$_3$) δ: 0.75 (3H, d, J=6.9 Hz), 0.80-0.96 (7H, m), 1.05 (1H, dq, J=3.8, 13.0 Hz), 1.13 (1H, q, J=11.8 Hz), 1.42-1.56 (2H, m), 1.63-1.75 (2H, m), 1.97 (1H, m), 2.08-2.17 (4H, m), 4.32 (1H, d, J=13.7 Hz), 4.73 (1H, d, J=13.7 Hz), 4.80 (1H, dt, J=4.6, 11.0 Hz), 6.09 (1H, t, J=6.9 Hz), 7.04 (1H, m), 7.16-7.24 (2H, m), 7.39 (1H, m), 7.48-7.58 (2H, m). MS(ESI-FTMS) m/z 516 [M+H]$^+$.

Example 2

Production of Compound (2)—2 (Production of Intermediate by Crystallization)

Triethylamine (3.00 mL, 21.8 mmol) was added to a solution of (±)-5-(3,4-difluorophenyl)-5-[(3-methyl-2-oxopyridin-1(2H)-yl)methyl]imidazolidin-2,4-dione (5.00 g, 15.0 mmol) in N,N-dimethylformamide (30.0 mL), and the mixture was stirred under ice cooling. (−)-Menthyl chloroformate (4.80 mL, 22.5 mmol) was added dropwise, and the mixture was stirred at room temperature for 1 hour. The reaction solution was filtered and washed with ethyl acetate. Ethyl acetate was distilled off under reduced pressure to obtain a solution containing the isomer mixture (1).
Methanol (30.0 mL) was added to the obtained solution containing the isomer mixture (1), and the mixture was stirred at room temperature for 1 hour. Water (6.0 mL) was added dropwise and the mixture was stirred at room temperature for 1 hour. The precipitated solid was collected by filtration and washed with methanol. Methanol (22.7 mL) was added to the obtained solid, and the mixture was stirred in a suspension state while heating under reflux. The mixture was allowed to cool at room temperature, and the solid was collected by filtration. The solid was washed with methanol, and then dried under reduced pressure to obtain compound (2) (2.44 g, 32% yield, 99.6% d.e.) as colorless solid.

Example 3

Production of Compound (2)—3 (Production of Intermediate by Solid-Liquid Separation)

Dimethyl sulfate (2.27 g, 18.0 mmol) was added dropwise to a solution of (1R,2S,5R)-2-isopropyl-5-methylcyclohexyl 1H-imidazole-1-carboxylate (4.50 g, 18.0 mmol) in acetonitrile (6.0 mL) at 50° C., and the mixture was stirred at 50° C. for 3.5 hours.

The obtained reaction solution was added dropwise to a solution of (±)-5-(3,4-difluorophenyl)-5-[(3-methyl-2-oxopyridin-1(2H)-yl)methyl]imidazolidin-2,4-dione (5.00 g, 15.0 mmol) and triethylamine (2.7 mL, 19.5 mmol) in acetonitrile (30.0 mL), and the mixture was stirred at 55° C. for 1.5 hours. The mixture was allowed to cool at room temperature to obtain a suspension including the isomer mixture (1).

The solid in the suspension including the obtained isomer mixture (1) was collected by filtration and washed with acetonitrile. The solid was then dried under reduced pressure to give compound (2) (3.24 g, 42% yield, 97.1% d.e.) as colorless solid.

Example 4

Production of (R)-5-(3,4-difluorophenyl)-5-[(3-methyl-2-oxopyridin-1(2H)-yl)methyl]imidazolidin-2,4-dione-1 (Method Using Acid)

Sulfuric acid (10.5 mol/L, 80.0 mL) was added to compound (2) (20.0 g, 38.8 mmol, 98.5% d.e.) to form a suspension. The suspension was stirred at 70° C. for 2 hours, and allowed to cool at room temperature. The suspension was then diluted with ethyl acetate and water. The organic layer was separated and washed with saturated brine. The solvent was distilled off under reduced pressure, and methyl ethyl ketone (60.0 mL) was added to the residue. The mixture was stirred under reflux to obtain a clear solution. Diisopropyl ether (240 mL) was added dropwise, and the mixture was allowed to cool at room temperature. The precipitated solid was collected by filtration, and washed with diisopropyl ether. The solid was dried under reduced pressure to give (R)-5-(3,4-difluorophenyl)-5-[(3-methyl-2-oxopyridin-1(2H)-yl)methyl]imidazolidin-2,4-dione (11.04 g, 85% yield, 98.8% e.e.) as colorless solid.

$^1$H-NMR (400 MHz, DMSO-$d_6$) δ: 1.98 (3H, s), 4.46 (1H, d, J=13.7 Hz), 4.61 (1H, d, J=13.7 Hz), 6.13 (1H, t, J=6.9 Hz), 7.22-7.33 (2H, m), 7.45-7.58 (2H, m), 7.69 (1H, ddd, J=2.3, 7.8, 12.4 Hz), 8.66 (1H, s), 10.99 (1H, s).

MS(ESI-FTMS) m/z 334 [M+H]$^+$.

The target compound was obtained at a higher production efficiency and at a lower cost than in the prior art methods.

Example 5

Production of (R)-5-(3,4-difluorophenyl)-5-[(3-methyl-2-oxopyridin-1(2H)-yl)methyl]imidazolidin-2,4-dione-2 (Method Using Base)

A solution of sodium ethoxide in ethanol (20%, 280 μL) was added to a suspension of compound (2) (200 mg, 0.388 mmol, 99.8% d.e.) in ethanol (3.0 mL), and the mixture was stirred at room temperature for 1.5 hours. The mixture was diluted with ethyl acetate and 1 mol/L hydrochloric acid, and the organic layer was separated. The organic layer was washed with saturated brine, and dried over anhydrous sodium sulfate. The solvent was distilled off under reduced pressure, and the residue was purified by column chromatography (silica gel) to obtain (R)-5-(3,4-difluorophenyl)-5-[(3-methyl-2-oxopyridin-1(2H)-yl)methyl]imidazolidin-2,4-dione (124 mg, 96% yield, 99.9% e.e.) as colorless solid.

The target compound was obtained at a higher production efficiency and at a lower cost than in the prior art methods.

The compound (1)-(S) ((S)-(1R,2S,5R)-2-isopropyl-5-methylcyclohexyl difluorophenyl)-4-[(3-methyl-2-oxopyridin-1(2H)-yl)methyl]-2,5-dioxoimidazolidine-1-carboxylate), which is a compound constituting the isomer mixture (1) together with compound (1)-(R), was synthesized by the method shown in the following Production Example 4, and the spectral data were confirmed.

Production Example 4

Production of Compound (1)-(S)

Triethylamine (2.50 mL, 18.0 mmol) was added to a solution of (S)-5-(3,4-difluorophenyl)-5-[(3-methyl-2-oxopyridin-1(2H)-yl)methyl]imidazolidin-2,4-dione (5.00 g, 15.0 mmol) in tetrahydrofuran (30.0 mL), and the mixture was stirred under ice cooling. A solution of (−)-menthyl chloroformate (3.82 mL, 18.0 mmol) in tetrahydrofuran (15.0 mL) was added dropwise, and the mixture was stirred for 5 minutes. The reaction solution was filtered, and the solvent was distilled off under reduced pressure. The residue was purified by column chromatography (silica gel) to obtain compound (1)-(S) (6.98 g, 90% yield) as colorless solid.

$^1$H-NMR (400 MHz, CDCl$_3$) δ: 0.74 (3H, d, J=6.9 Hz), 0.85-0.92 (7H, m), 1.00-1.15 (2H, m), 1.46-1.53 (2H, m), 1.67-1.73 (2H, m), 1.98 (1H, m), 2.10-2.12 (4H, m), 4.32 (1H, d, J=13.8 Hz), 4.71 (1H, d, J=13.8 Hz), 4.79 (1H, dt, J=4.4, 10.9 Hz), 6.10 (1H, t, J=6.8 Hz), 7.04 (1H, m), 7.16-7.23 (2H, m), 7.37 (1H, m), 7.48-7.53 (2H, m).

MS(ESI-FTMS) m/z 516 [M+H]$^+$.

Meanwhile, the (S)-5-(3,4-difluorophenyl)-5-[(3-methyl-2-oxopyridin-1(2H)-yl)methyl]imidazolidin-2,4-dione of this production example denotes the same compound as the (−)-5-(3,4-difluorophenyl)-5-[(3-methyl-2-oxopyridin-1(2H)-yl)methyl]imidazolidin-2,4-dione described in Patent Literature 1.

Analysis Conditions and Calculation Method of Diastereomeric Excess of Compound (2)

The analysis conditions and the calculation method used in determining the diastereomeric excess of compound (2) described above are shown below.

[Analysis Conditions]

Column: CHIRALPAK (registered trademark) AD-H (4.6× 250 mm)

Eluent: Acetic acid:ethanol=1:1000

Flow rate: 0.5 mL/min

Retention time: Compound (1)-(R)=11.2 min, compound (1)-(S)=8.9 min

[Calculation Method]

The diastereomeric excess of compound (1)-(R) was calculated using the following equation based on the area percentage of compound (1)-(R) and compound (1)-(S) obtained from the above analysis conditions.

Diastereomeric excess (% d.e.) =

$$\frac{[\text{peak area (\%) of "compound (1)-}(R)\text{"}] - [\text{peak area (\%) of "compound (1)-}(S)\text{"}]}{[\text{peak area (\%) of "compound (1)-}(R)\text{"}] + [\text{peak area (\%) of "compound (1)-}(S)\text{"}]} \times 100$$

Analysis Conditions and Calculation Method of Optical Purity of (R)-5-(3,4-difluorophenyl)-5-[(3-methyl-2-oxopyridin-1(2H)-yl)methyl]imidazolidin-2,4-dione The analysis conditions and the calculation method used in determining the optical purity of (R)-5-(3,4-difluorophenyl)-5-[(3-methyl-2-oxopyridin-1(2H)-yl)methyl]imidazolidin-2,4-dione described above are shown below.
[Analysis Conditions]
Column: CHIRALPAK (registered trademark) AD-H (4.6× 250 mm)
Eluent: Normal hexane:ethanol=40:60
Flow rate: 0.5 mL/min
Retention time: (R) form=14.4 min, (S) form=33.8 min
[Calculation Method]
The enantiomeric excess of (R)-5-(3,4-difluorophenyl)-5-[(3-methyl-2-oxopyridin-1(2H)-yl)methyl]imidazolidin-2,4-dione was calculated using the following equation based on the area percentage of (R)-5-(3,4-difluorophenyl)-5-[(3-methyl-2-oxopyridin-1(2H)-yl)methyl]imidazolidin-2,4-dione and its enantiomer ((S) form) obtained from the above analysis conditions.

$$\text{Enantiomeric excess (\% e.e.)} = \frac{[\text{peak area (\%) of }(R)\text{ form}] - [\text{peak area (\%) of }(S)\text{ form}]}{[\text{peak area (\%) of }(R)\text{ form}] + [\text{peak area (\%) of }(S)\text{ form}]} \times 100$$

Comparative Test Example 1

Diastereomer mixtures (5a) to (5i) shown in Table 1 were synthesized and evaluated the separability of each isomer under recrystallization conditions. Diastereomer mixtures (5a) to (5i) are mixtures of diastereomers described in the following general formula (5) having the respective $R_{aux}$ groups shown in Table 1.

Figure 1A:
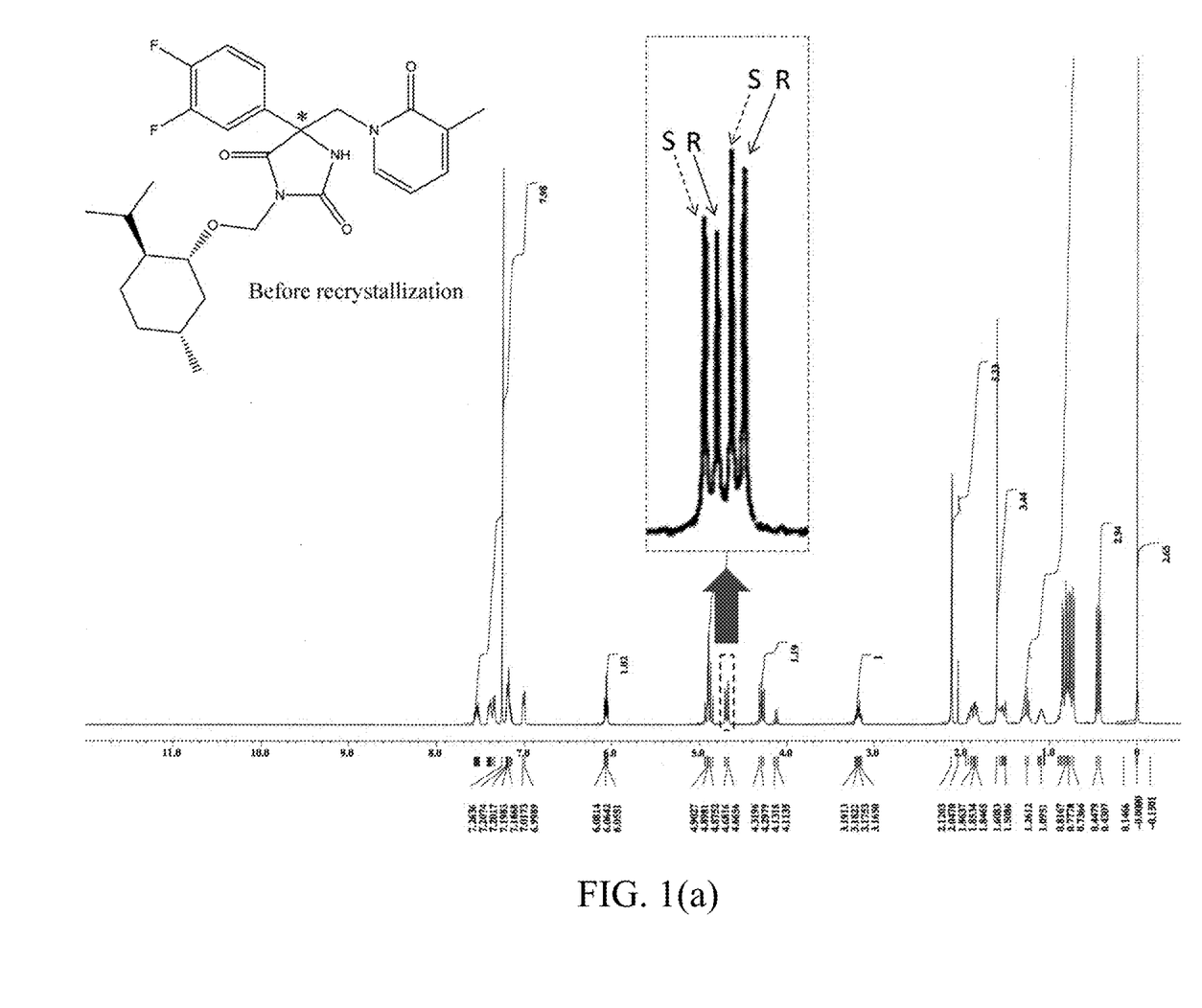
FIGS. 1(a) and 1(b) are $^1$H-NMR spectrum chart examples used for evaluating separability of the diastereomer mixture in Comparative Test Example 1, which is an example in which the diastereomer mixture was determined to be "Separable". The solid line arrow in the enlarged view shows a signal derived from a compound in which the stereochemistry of the asymmetric carbon indicated by * in the chemical formula shown in these figures is the (R) form, and the broken line arrow shows a signal derived from a compound whose configuration is the (S) form. The chart in FIG. 1(a) is a chart before recrystallization, and the chart in FIG. 1(b) is a chart after recrystallization.
Figure 1B:
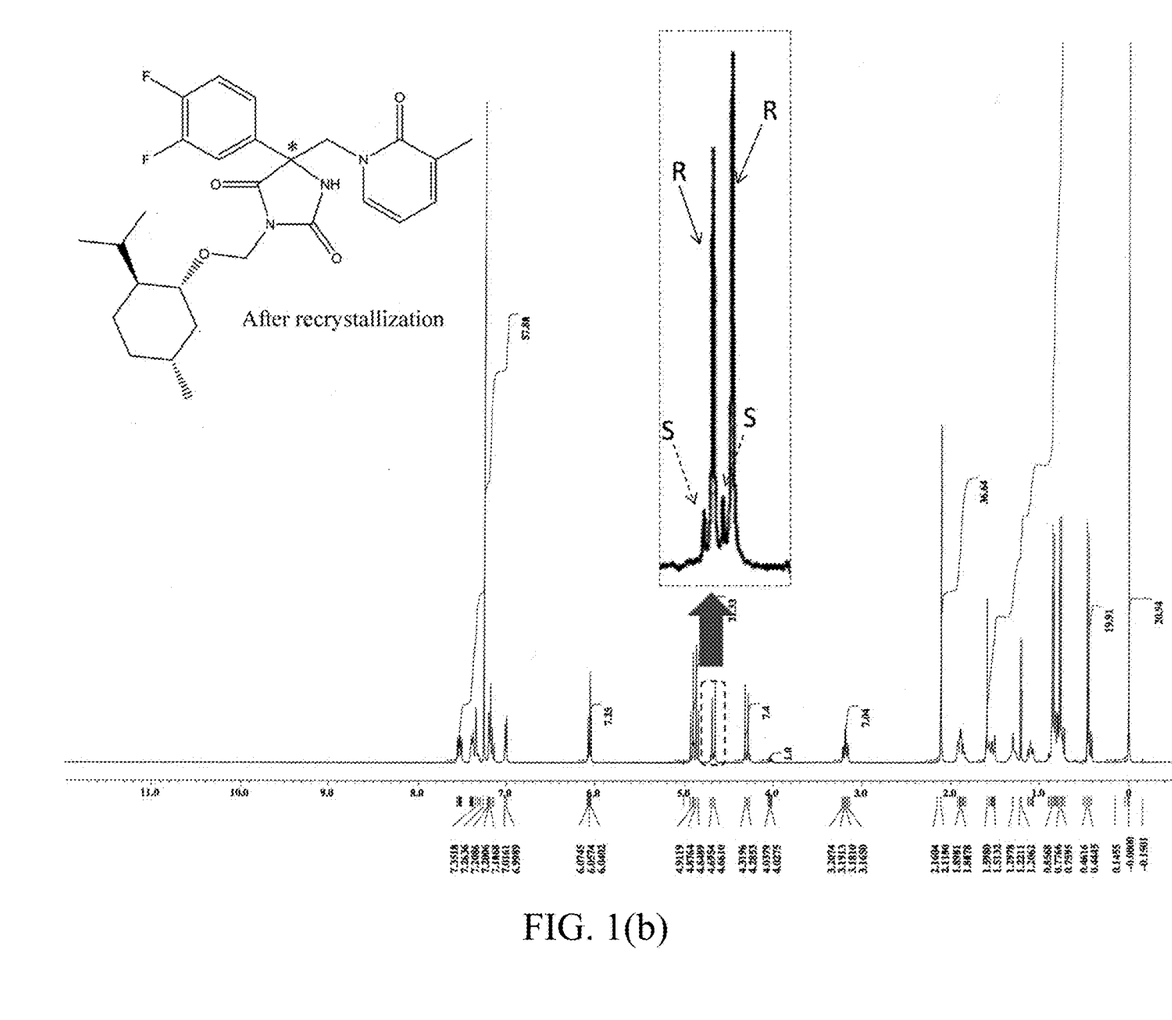
Figure 2A:
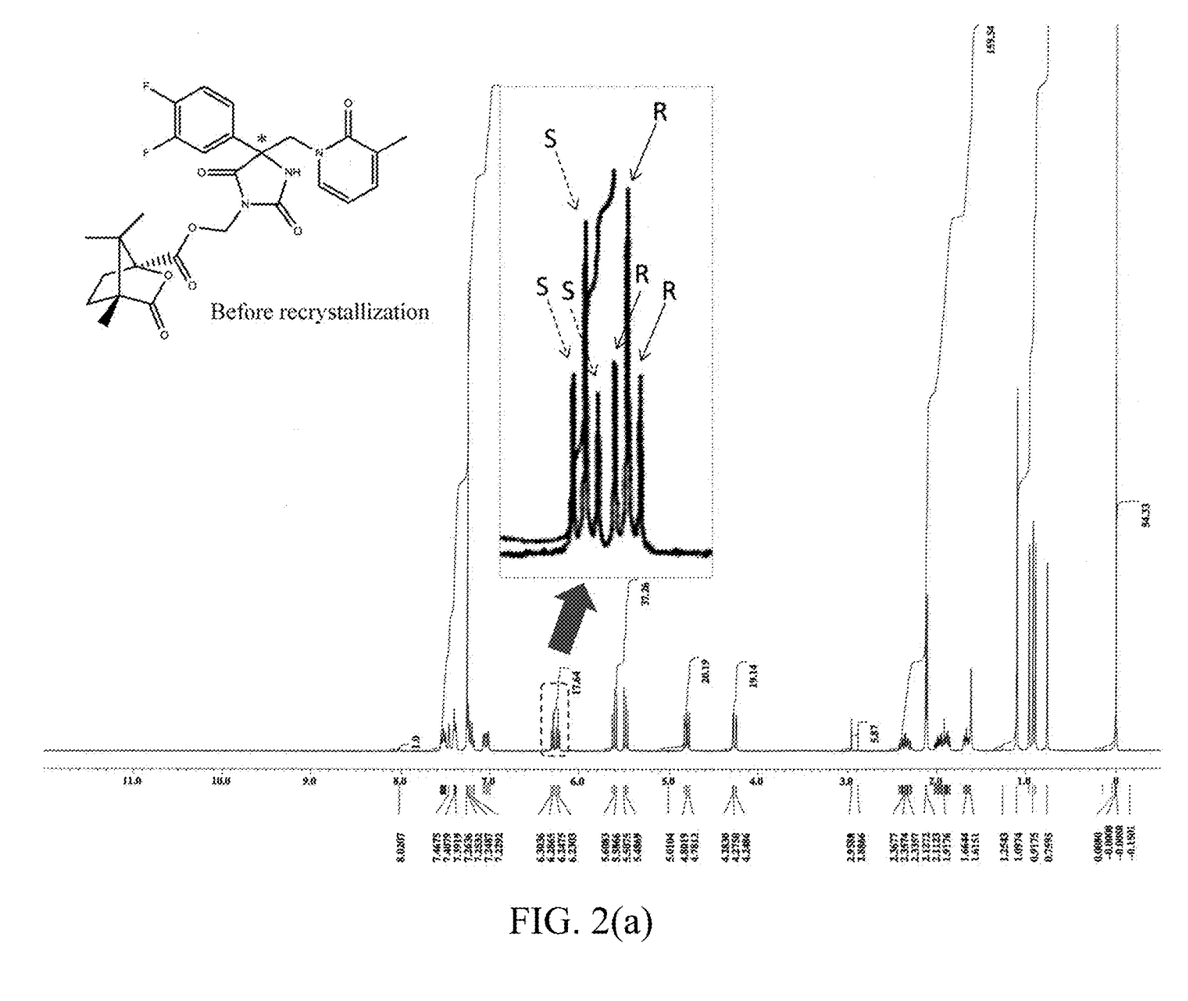
FIGS. 2(a) and 2(b) are $^1$H NMR spectrum chart examples used for evaluating separability of the diastereomer mixture in Comparative Test Example 1, which is an example in which the diastereomer mixture was determined to be "Inseparable". The solid line arrow in the enlarged view shows a signal derived from a compound in which the stereochemistry of the asymmetric carbon indicated by * in the chemical formula shown in these figures is the (R) form, and the broken line arrow shows a signal derived from a compound whose configuration is the (S) form. The chart in FIG. 2(a) is a chart before recrystallization, and the chart in FIG. 2(b) is a chart after recrystallization.
Figure 2B:
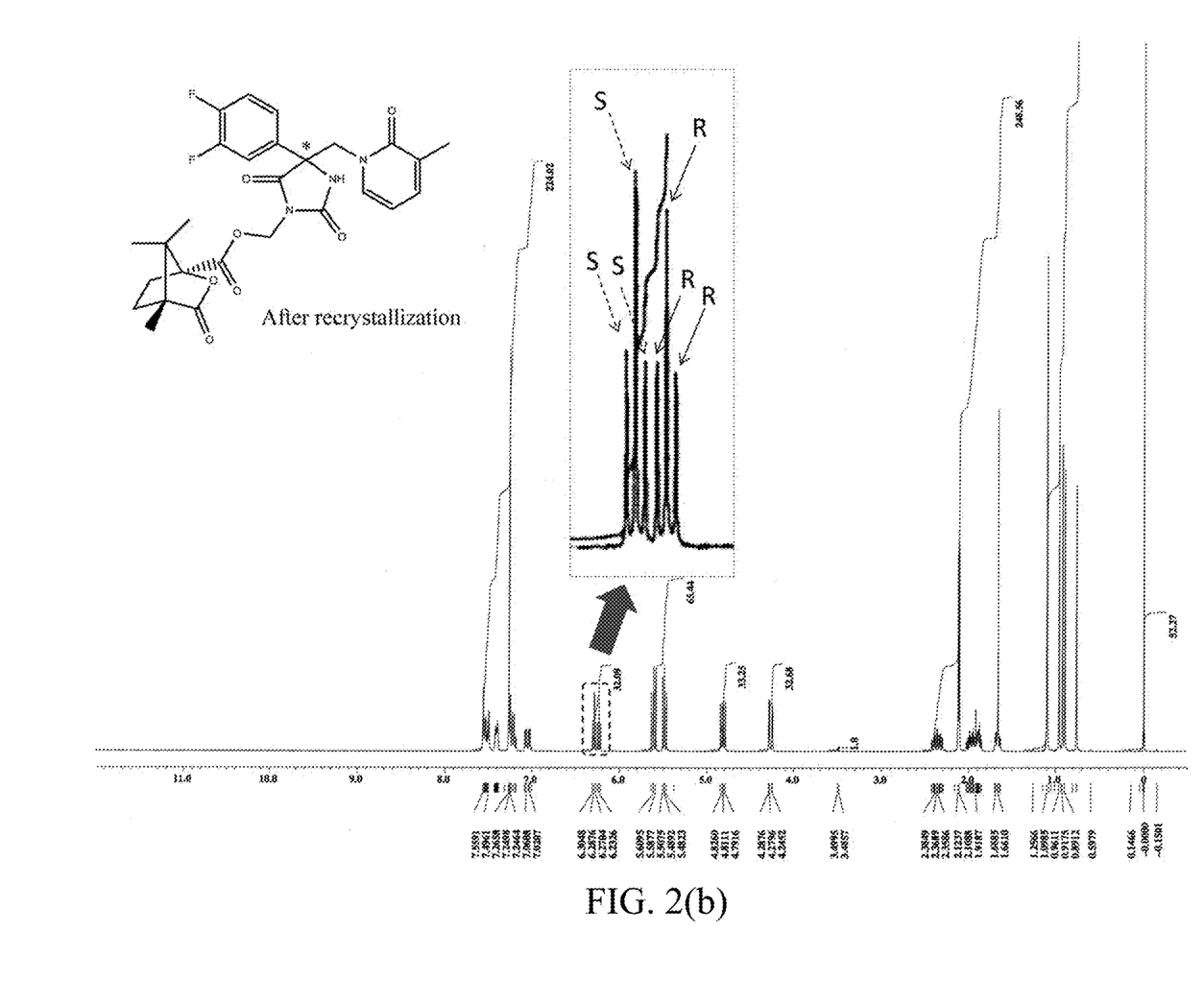

The separability was evaluated by the ease of recrystallization and the $^1$H-NMR spectrum of the product obtained by recrystallization. For example, as shown in FIGS. 1(a) and 1(b), the diastereomer mixture was determined to be "Separable" in the case of that the signal intensity derived from each isomer in the $^1$H-NMR spectrum was largely different between before recrystallization (FIG. 1(a)) and after recrystallization (FIG. 1(b)). In contrast, the diastereomer mixture was determined to be "Inseparable" in the case of that recrystallization was difficult or the case, as shown in FIGS. 2(a) and (b), of that the signal intensity derived from each isomer in the $^1$H-NMR spectrum was almost no different between before recrystallization (FIG. 2(a)) and after recrystallization FIG. 2(b)).

The results on the separability of each diastereomer mixture are shown in Table 1.

TABLE 1

(5)

| $R_{aux}$ | Separability |
|---|---|
| (5a) | Inseparable |
| (5b) | Inseparable |
| (5c) | Inseparable |
| (5d) | Inseparable |
| (5e) | Inseparable |
| (5f) | Inseparable |

TABLE 1-continued

| $R_{aux}$ | Separability |
|---|---|
|  (5g) | Inseparable |
|  (5h) | Separable |
|  (5i) | Separable |

As is apparent from the results in Table 1, it was shown that the mixtures with a menthyl group (5h and 5i) have remarkably good separability.

Comparative Test Example 2

The separability of the two mixtures that showed good results in Comparative Test Example 1 (5h and 5i) was examined in more detail by testing under various conditions. As a result, for the mixture (5h) having a menthyloxymethyl group ((1R,2S,5R)-2-isopropyl-5-methylcyclohexyloxymethyl group), when the separated product was obtained with 70% or more diastereomeric excess, the yield was less than 15% in each condition. More specifically, in terms of both view point of yield and diastereomeric excess, the mixture (5i) having menthyloxycarbonyl group exhibited better results than the mixture (5h) having menthyloxymethyl group.

Therefore, it was shown that the separability of the isomer mixture (1) of the present invention (i.e., the above-mentioned diastereomer mixture (5i)) is particularly excellent.

INDUSTRIAL APPLICABILITY

The (R)-5-(3,4-difluorophenyl)-5-[(3-methyl-2-oxopyridin-1(2H)-yl)methyl]imidazolidin-2,4-dione obtained by the production method of the present invention is useful as, for example, a prophylactic or a therapeutic agent, for diseases involving TNF-α (see, for example, Patent Literature 1), and according to the production method of the present invention, that target compound can be obtained more simply and efficiently than by methods of the prior art. Further, according to the present invention, there is also provided intermediates suitably used for the above-mentioned method for producing the target compound, and it is also possible to efficiently produce the target compound on a commercial scale.

Therefore, the present invention will greatly contribute to the progress of the pharmaceutical and related industries.

The invention claimed is:

1. A method of producing (R)-5-(3,4-difluorophenyl)-5-[(3-methyl-2-oxopyridin-1(2H)-yl)methyl]imidazolidin-2,4-dione, the method comprising:
(a) a step of separating an isomer represented by the following formula (2)

from a mixture of isomers represented by the following formula (1); and (b) a step of removing menthyloxycarbonyl group of the compound represented by formula (2) separated in step (a) to obtain (R)-5-(3,4-difluorophenyl)-5-[(3-methyl-2-oxopyridin-1(2H)-yl)methyl]imidazolidin-2,4-dione.

2. The method according to claim 1, wherein the mixture of isomers represented by formula (1) is obtained from a racemate (±)-5-(3,4-difluorophenyl)-5-[(3-methyl-2-oxopyridin-1(2H)-yl)methyl]imidazolidin-2,4-dione.

3. (R)-(1R,2S,5R)-2-isopropyl-5-methylcyclohexyl 4-(3,4-difluorophenyl)-4-[(3-methyl-2-oxopyridin-1(2H)-yl)methyl]-2,5-dioxoimidazolidine-1-carboxylate.

\* \* \* \* \*